United States Patent
Roh (10) Patent No.: US 11,033,206 B2
(45) Date of Patent: Jun. 15, 2021

(54) SYSTEM, APPARATUS, AND METHOD FOR MONITORING AND PROMOTING PATIENT MOBILITY

(71) Applicant: Circulex, Inc., Seattle, WA (US)

(72) Inventor: Jeffrey Roh, Seattle, WA (US)

(73) Assignee: Circulex, Inc., Seattle, WA (US)

( * ) Notice: Subject to any disclaimer, the term of this patent is extended or adjusted under 35 U.S.C. 154(b) by 0 days.

(21) Appl. No.: 15/612,873

(22) Filed: Jun. 2, 2017

(65) Prior Publication Data

US 2017/0347923 A1 Dec. 7, 2017

Related U.S. Application Data

(60) Provisional application No. 62/345,651, filed on Jun. 3, 2016.

(51) Int. Cl.
| | |
|---|---|
| *A61B 5/11* | (2006.01) |
| *A61B 5/00* | (2006.01) |
| *A61N 1/36* | (2006.01) |
| *A61F 13/84* | (2006.01) |
| *A61F 13/00* | (2006.01) |
| *G16H 40/67* | (2018.01) |

(52) U.S. Cl.
CPC ............ *A61B 5/1118* (2013.01); *A61B 5/002* (2013.01); *A61B 5/0022* (2013.01); *A61B 5/6831* (2013.01); *A61B 5/7405* (2013.01); *A61B 5/746* (2013.01); *A61B 5/7455* (2013.01); *A61F 13/00051* (2013.01); *A61F 13/84* (2013.01); *A61N 1/36014* (2013.01); *G16H 40/67* (2018.01); *A61B 2505/09* (2013.01); *A61B 2562/0219* (2013.01); *A61F 2013/8473* (2013.01)

(58) Field of Classification Search
CPC ....... A61B 5/682; A61B 5/02007; A61B 5/11; A61B 5/1113–1114; A61B 5/1116; A61B 5/1118; A61L 35/11
See application file for complete search history.

(56) References Cited

U.S. PATENT DOCUMENTS

| | | | |
|---|---|---|---|
| 6,226,552 B1 | 5/2001 | Staunton et al. | |
| 6,298,314 B1* | 10/2001 | Blackadar | A61B 5/1121 235/105 |
| 10,098,572 B2* | 10/2018 | Schwenk | A61B 5/1118 |
| 2005/0033200 A1* | 2/2005 | Soehren | A61B 5/0002 600/595 |
| 2006/0288464 A1* | 12/2006 | Warden | A41D 13/0506 2/69 |

(Continued)

FOREIGN PATENT DOCUMENTS

EP          1834580 A1 *   9/2007  ............... A61B 5/11

*Primary Examiner* — Matthew Kremer
(74) *Attorney, Agent, or Firm* — Perkins Coie LLP (57) ABSTRACT

A method is provided which includes providing a sensor operable to measure movement over time on a user. The sensor includes an alert unit. The sensor is configured with a threshold to activate the alert unit when the measured movement over time is below the threshold. The measurements of movement over time are obtained, and it is determined whether the measured movement over time is below the threshold. When the measured movement is below the threshold, the alert unit at the sensor is activated to alert the user.

22 Claims, 8 Drawing Sheets

(56) References Cited

U.S. PATENT DOCUMENTS

| | | | |
|---|---|---|---|
| 2008/0214360 A1* | 9/2008 | Stirling | A61B 5/1118 482/9 |
| 2010/0165290 A1* | 7/2010 | Shea | A61B 3/1015 351/205 |
| 2012/0065561 A1* | 3/2012 | Ballas | A61H 9/0021 601/152 |
| 2012/0253142 A1* | 10/2012 | Meger | A61B 5/1116 600/301 |
| 2014/0200474 A1* | 7/2014 | Selvaraj | A61B 5/0806 600/529 |
| 2014/0303460 A1* | 10/2014 | Corley | A61B 5/6828 600/301 |
| 2015/0109442 A1* | 4/2015 | Derenne | G08B 21/245 348/143 |
| 2016/0192890 A1* | 7/2016 | Averina | A61B 5/021 600/481 |
| 2016/0203691 A1* | 7/2016 | Arnold | G08B 21/0415 340/539.12 |
| 2016/0331303 A1* | 11/2016 | Shen | A61B 5/14542 |
| 2016/0339300 A1* | 11/2016 | Todasco | G06F 19/3481 |
| 2017/0080151 A1* | 3/2017 | Cerny | G16H 40/63 |
| 2017/0172448 A1* | 6/2017 | Shin | A61B 5/0022 |
| 2017/0281075 A1* | 10/2017 | Younker | A61B 5/486 |
| 2018/0235537 A1* | 8/2018 | Whiting | A61B 5/4836 |

\* cited by examiner

SYSTEM, APPARATUS, AND METHOD FOR MONITORING AND PROMOTING PATIENT MOBILITY

CROSS-REFERENCE TO RELATED APPLICATION

This application claims priority to U.S. Provisional Patent Application No. 62/345,651, filed in the U.S. Patent and Trademark Office on Jun. 3, 2016, all of which is incorporated herein by reference in its entirety for all purposes.

FIELD

The present disclosure relates generally to systems and methods for monitoring and promoting patient mobility.

BACKGROUND

Deep vein thrombosis (DVT) is the formation of blood clots within a deep vein, most commonly in the lower extremities, and is a serious medical condition. This can develop into an even more serious condition called pulmonary embolism (PE), which is a blockage caused by blood clots in the vascular system within the lungs that can prove to be fatal. Patients who are hospitalized are at an increased risk for both DVT and PE, which together are known as venous thromboembolism (VTE).

The Centers for Disease Control (CDC) estimates that as many as 900,000 people are affected by DVT/PE each year in the United States. Their estimates suggest that up to 100,000 Americans per year die of DVT/PE, and up to 30% of people will die within one month of diagnosis. Sudden death is the first symptom in about 25% of people who have a PE.

DVT in the leg is the most common cause. A blood clot can come loose from the vein and move through the bloodstream so that the blood clot ends up partially or completely blocking a lung artery, leading to PE. This can happen right after the clot forms, or it may happen later.

At least 1 in 10 people with DVT have a PE. That number may be much higher, though, because 3 out of 4 cases of DVT cause no symptoms and go undiagnosed. Symptoms that are associated with PE are (1) a sudden cough, which may be bloody; (2) rapid breathing or sudden shortness of breath, even while resting; (3) chest pain: sharp or stabbing, burning, aching, or dull (might get worse with deep breaths, coughing, eating, or bending); (4) sudden rapid heart rate or irregular heartbeat (heart palpitations); (5) heart failure, when the heart cannot keep up with the body's demands; (6) difficulty breathing; or (7) high blood pressure in the lung arteries, called pulmonary hypertension.

When a clot stays in the leg or arm for too long, it can damage the vein or its valves. Valves that do not function correctly let blood backflow and pool, instead of pushing the blood toward the heart. Post thrombotic syndrome is usually mild, but some symptoms can be severe; the symptoms may not show up until years later. About half of people with DVT end up with long-term effects where the clot caused (1) pain, (2) swelling, (3) darkened skin color, or (4) varicose veins, which are swollen, sometimes twisted or blue veins that can be seen under the skin. Because blood that is not flowing well is more likely to clot, the probability of another DVT or a pulmonary embolism becomes greater.

Prevention is key and a doctor may recommend: (1) wearing compression stockings, (2) keeping legs or arms raised while at rest, (3) undergoing a procedure that opens a narrow vein, such as a balloon angioplasty or stenting, or (4) getting the clot removed with surgery.

Another risk factor for developing these serious vascular conditions is post-operative patients who are relatively immobile. As a point of reference, the incidence of DVT in patients who have undergone total knee replacement can be as high as 60%. In a study of almost 500,000 surgeries performed in Department of Veterans Affairs (VA) hospitals from 2005 to 2010, approximately 1% of patients developed a VTE within 90 days. Approximately 60% of VTEs following surgery occurred up to 90 days after the patient left the hospital. Of the patients who developed VTEs, approximately 80% were readmitted to a hospital. Per the CDC, using hospital discharge data alone to track how often VTE occurs after surgery leads to an understatement of the true size and scope of the problem.

The three main factors that are known causes of DVT are hemodynamic stasis (slow blood flow), hypercoagulability (abnormality of blood coagulation), and endothelial injury to the vascular wall. The mainstays of non-pharmacologic prevention of DVTs have historically consisted of (1) thromboembolism deterrent (TED) stockings and (2) sequential compression devices (SCDs).

TED stockings or "compression stockings" are specialized hosiery designed to help prevent the occurrence of, and guard against further progression of, venous disorders such as edema, phlebitis and thrombosis. Compression stockings are elastic garments worn around the leg, compressing the limb. Compression stockings reduce the diameter of distended veins and increase venous blood flow velocity and valve effectiveness. Compression stockings used as therapy help decrease venous pressure, prevent venous stasis and impairments of venous walls, and relieve heavy and aching legs.

There are various types of TED stockings such as "knee-high compression stockings" which are used not only to help increase circulation, but also to help prevent the formation of blood clots in the lower legs. Knee-high compression stockings also aid in the treatment of ulcers of the lower legs.

Unlike regular stockings, TED compression stockings use stronger elastics to create significant pressure on the legs, ankles and feet. Compression stockings are tightest at the ankles and gradually become less constrictive toward the knees and thighs. TED stockings provide a graduated pressure gradient with more pressure near the ankle and progressively less pressure near the knee. By compressing the surface veins, arteries and muscles, the compression stockings force circulating blood through narrower channels. Thus, the arterial pressure is increased, which causes more blood to return to the heart and less blood to pool in the feet.

Although this type of treatment has been found to be relatively effective in decreasing the amount of pain, swelling, and clinical scores in patients with DVT and post-thrombotic syndrome, TED stockings have limitations and have not been shown to be preventative. In addition, TED stockings have limitations in that they are low-tech commodity items that do not give health care providers the ability to monitor the immobility and subsequent risk of developing DVTs in their patients. TED stockings have other limitations in that their use are not regulated by the users, for instance some users may wear the TED stockings all the time, while others only at certain times of the day.

Further complications of use of TED stockings are (1) the creation of pressure areas and ulcers if poorly fitted; (2) inadequate function if incorrectly sized or too loose; (3) risk of falling if the patient mobilizes on a slippery surface; or (4) DVT if inappropriately used alone in high risk patients.

For TED stockings to be effective, they must fit properly. If they are too large, the patient's lower extremities will not be supported properly and too little compression will be applied. If they are too small, they can impair circulation in the lower extremities, resulting in injury.

To ensure that patients are wearing the proper size TED stockings, the circumference of the leg is measured with a tape measure at various points along the leg. The measurements are compared to those on the sizing chart such that the correct size elastic stocking is selected.

Sequential compression devices (SCDs) are a pair of lower extremity sleeves with air pockets connected to an air compressor that sequentially forces air into the pockets of the sleeves. The intended effect that the filling of the pockets has on the lower extremities is to "milk" the flow of blood back to the heart by sequentially squeezing the blood from the ankles to the knees.

SCDs provide intermittent compression to the lower extremities to promote venous return and to help prevent DVT. They can be applied to one or both lower extremities, depending on the patient's specific needs. SCDs are contraindicated for patients who have severe arterial disease.

SCDs are available in either knee length or thigh length and consist of an air pump, connection tubing, and sleeves that fit over or around the lower extremity. The provider generally specifies the amount of compression to apply.

For elastic stockings and sequential compression devices to be effective, they must fit properly. Limitations of SCDs include that if they are too large, the patient's lower extremities will not be supported properly and too little compression will be applied. If they are too small, they can impair circulation in the lower extremities, resulting in injury.

Another limitation with SCDs is that it is complicated to ensure that patients are wearing the proper size elastic stockings, will measure the circumference of the leg with a tape measure at various points along the leg and that the measurements are manually compared to a "sizing chart" to select the correct size elastic stocking.

Another limitation is that to determine the correct size of an SCD sleeve, the patient is measured, and, once the compression sleeve is in place, the SCD sleeve is manually checked for fit by placing two fingers between the sleeve and the patient's leg. If two fingers do not fit, the sleeve is too small, thus allowing for user interpretation (which can vary) for fit.

SCDs provide intermittent compression to the lower extremities to promote venous return and to help prevent DVT. They can be applied to one or both lower extremities, depending on the patient's specific needs. SCDs are contraindicated for patients who have severe arterial disease.

For patients who wear TED stockings or SCDs, it is important to remove the TED stockings or SCDs at least every 8 hours, or per the facility's policy, and to assess skin condition and circulatory status.

It is also important to educate patients about the proper use and fit of these stockings and devices. The top of the stockings should not be rolled down and the toe openings should not be pulled back over the foot since either can impede circulation. The SCD's tubing and connection sites should not be placed underneath the leg, since this can increase the risk of pressure ulcers and of device malfunction.

Although SCDs have been found to be relatively effective in reducing the incidence of DVTs, the SCDs have limitations in that the wearer cannot be mobile since the air compressor is large and must be plugged into a wall outlet. Additionally, another limitation is that SCDs are expensive (thousands of dollars) and are high maintenance. Other limitations are that the patient usually cannot take the SCD with them once they are discharged from the hospital, thereby precluding its use outside of the hospital environment. Finally, SCDs have limitations in that they do not give health care providers the ability to monitor the immobility and subsequent risk of developing DVTs in their patients.

Another limitation for TED stockings and SCD stockings is that it is important for the user to remember to remove them at least every 8 hours to assess skin condition and circulatory status.

Another limitation is that users need to be educated about the proper use and fit of these stockings and devices, in that the user should not roll the top of the stockings down or pull the toe openings back over the foot since either can impede circulation.

Thus, there is a need in the art for a solution that overcomes these and other limitations of TED stockings and SCDs.

BRIEF DESCRIPTION OF THE DRAWINGS

In the detailed description that follows, embodiments are described as illustrations only since various changes and modifications will become apparent to those skilled in the art from the following detailed description.

DETAILED DESCRIPTION

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

Figure 1A:
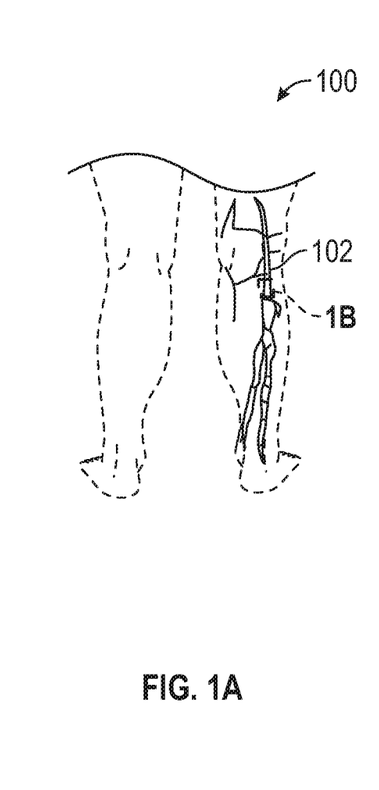
FIGS. 1A-1D show visual diagrams of the progression from deep vein thrombosis to venous thromboembolism.
Figure 1B:
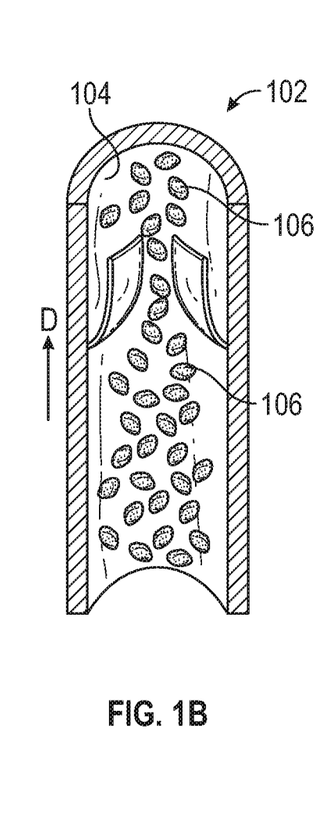
Figure 1C:
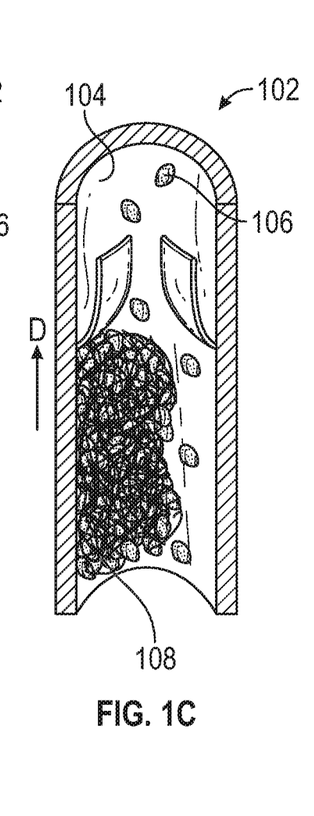
Figure 1D:
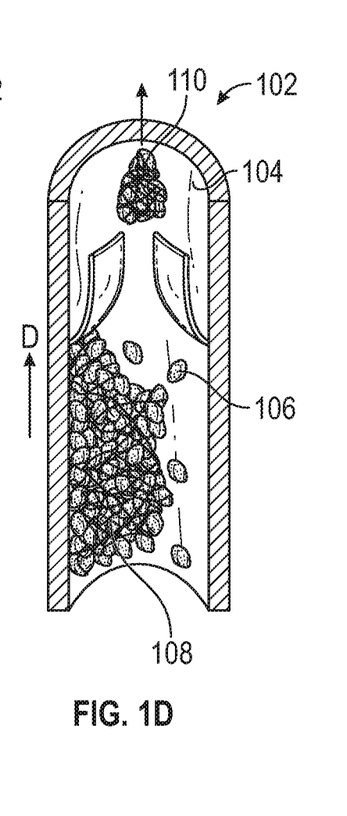

FIGS. 1A-1D show a visual diagram of the progression from deep vein thrombosis (DVT) to venous thromboembolism (VTE). FIG. 1A illustrates the deep veins 102 of the leg 100. While a leg 100 is illustrated, DVT can occur in other veins in the body. FIG. 1B shows an enlarged view of a vein 102. The vein 102 in FIG. 1B is normal, in that the vein 102 does not have a blood clot. The vein 102 has a wall 104 which provides a passage for blood cells 106 to pass therein. The blood cells 106, as shown in FIG. 1B, travel in the direction D. As there is no blood clot in the vein shown in FIG. 1B, the blood cells 106 travel without impedance. FIG. 1C shows an example of deep vein thrombosis. A blood clot 108 is formed along the wall 104 of the vein 102. When at least a piece of the blood clot 108 breaks loose and travels in the blood 106, this is called a venous thromboembolism (VTE). The abbreviation DVT/PE refers to a VTE where a deep vein thrombosis (DVT) has moved to the lungs (pulmonary embolism or PE). FIG. 1D shows an embolus 110 that has escaped through a vein 102. Since the veins 102 return blood 106 to the heart, if a piece 110 of a blood clot 108 formed in a vein 102 breaks off, the piece 110 can be transported to the right side of the heart, and from there into the lungs. A piece of thrombus 108 that is transported in this way is an embolus 110: the process of forming a thrombus 108 that becomes embolic is called a thromboembolism. An embolism that lodges in the lungs is a pulmonary embolism (PE). A pulmonary embolism is a very serious condition that can be fatal depending on the dimensions of the embolus 110. VTE refers to both DVTs and PEs. Embodiments of the present disclosure promote patient mobility and encourage blood flow, which may help reduce the risk factors for DVT.

Figure 2:
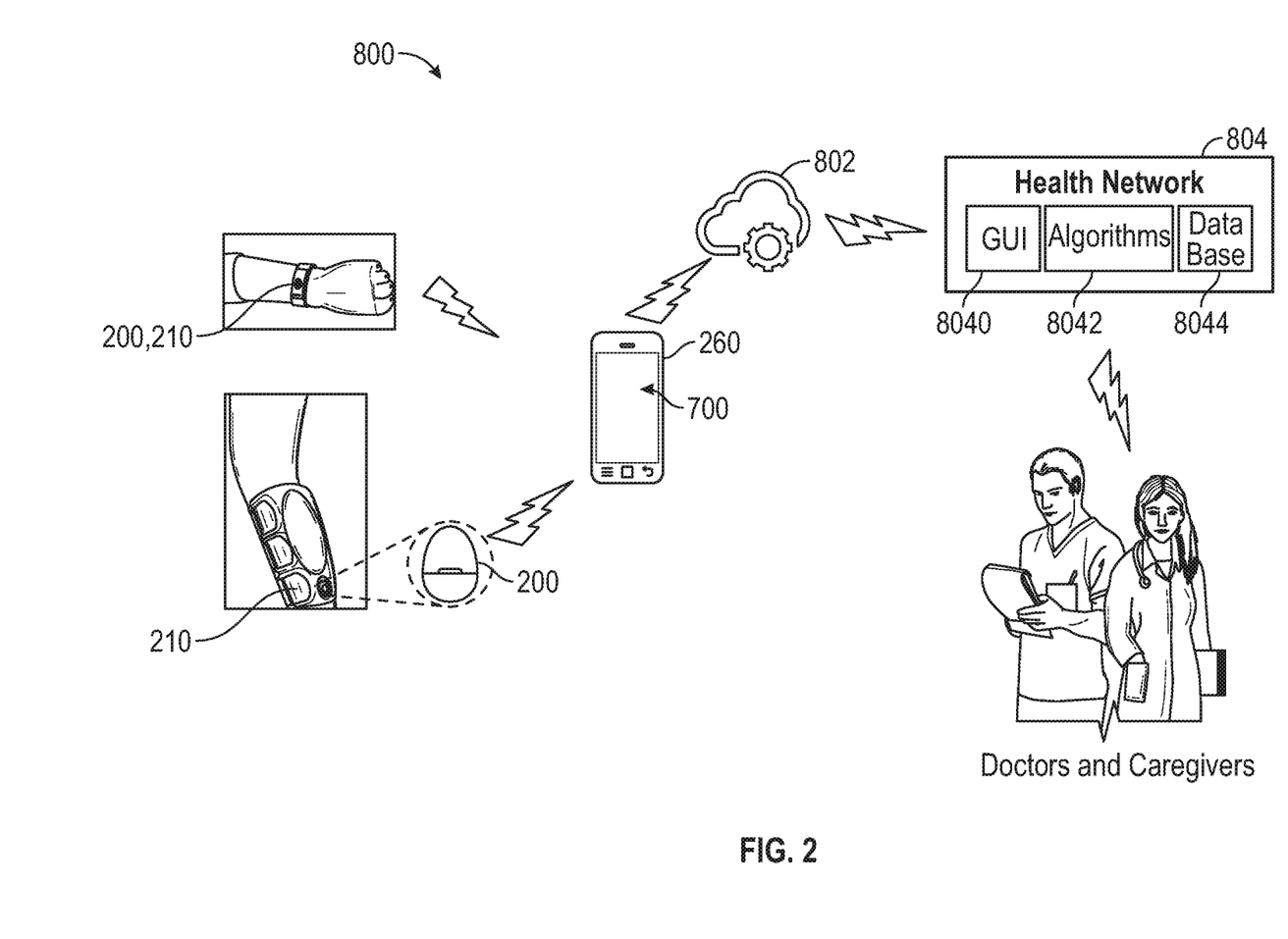
FIG. 2 illustrates an exemplary system by which at least aspects of monitoring and promoting patient mobility may be implemented.
Figure 3A:
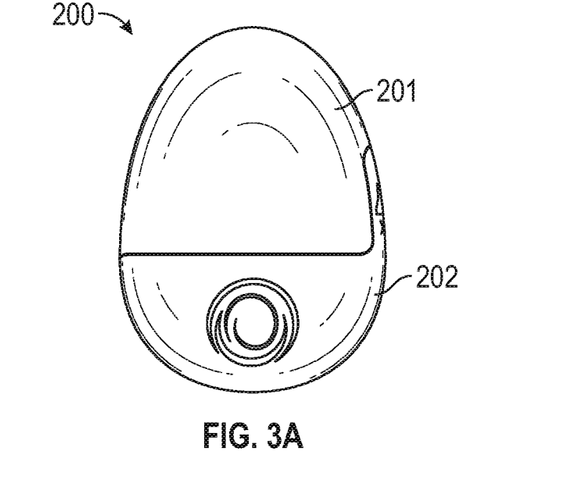
FIGS. 3A-3F show an exemplary sensor by which at least aspects of monitoring and promoting patient mobility may be implemented.
Figure 3B:
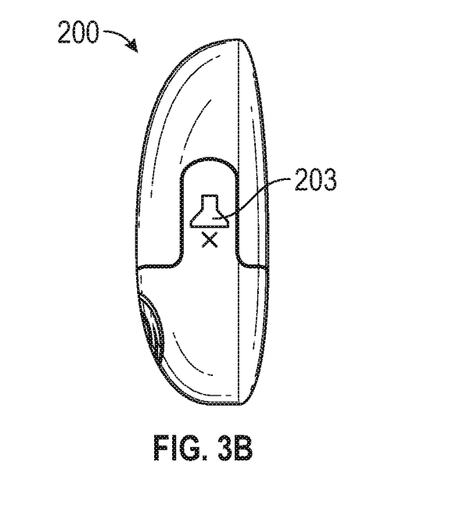
Figure 3C:
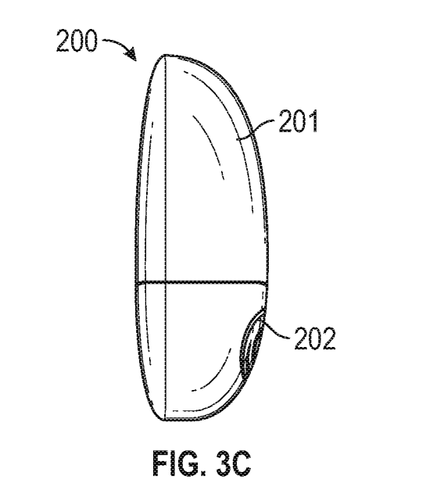
Figure 3D:
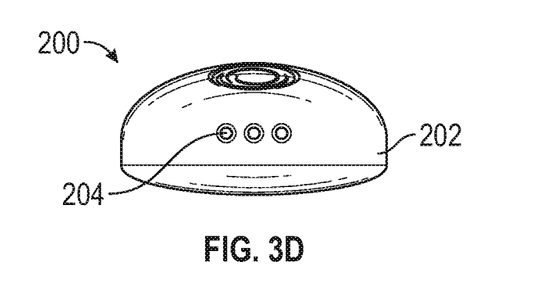
Figure 3E:
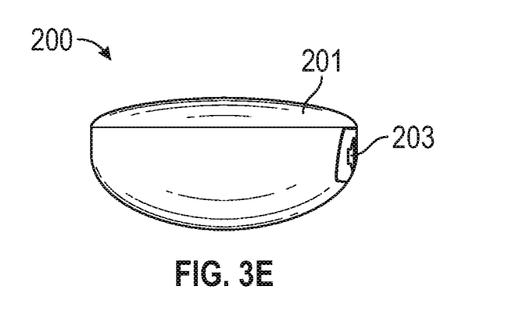
Figure 3F:
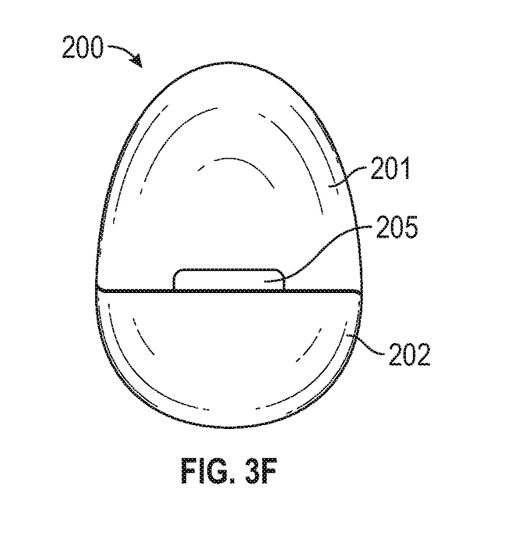

FIG. 2 illustrates a system for using a sensor 200. The sensor 200 can be operable to be inserted into a wearable 210, for example a compression sleeve or a compression sock. In other examples, the sensor 200 can be built into the wearable 210, for example a band that can be worn around the ankle or wrist or built into a compression sleeve or sock. The sensor 200 can be inserted and/or attached to the wearable 210 by, but is not limited to, (1) having a small holder or pocket in the wearable 210 adapted to fit the sensor 200, (2) having the sensor 200 fit snugly under the wearable 210 without a holder, (3) having a fabric attachment (for example, Velcro), with one attachment coupled with the sensor 200 and one attachment coupled with the wearable 210, and (4) having the wearable 210 have a split opening capable of receiving the sensor 200.

The sensor 200 and/or the wearable 210 can also be used to communicate with other features, for example GPS, devices 260, cloud computing 802, or any other features. The sensor 200 can be communicatively coupled with and communicate directly with the other features such as cloud computing 802, or can communicate through a device 260 which then can communicate the information to cloud computing 802. The sensor 200 can communicate to the device 260 by direct communication, such as USB, and/or by wireless communication, such as WiFi, the Internet, and BLUETOOTH. In other examples, the sensor 200 and/or the wearable 210 can perform at least one function, for example measure heart rate, measure time, assess acceleration, assess velocity, and assess orientation. The sensor 200 tracks and calculates the movement of the user. The wearable 210 can also include a neuromuscular electrical stimulation (NMES) unit to provide electrical pulses to the muscle.

The device 260 has a graphical user interface (GUI). The device 260 connects to cloud computing which connects to a network that communicates with another device which contains a GUI (not shown that can allow the doctor and caregivers to upload and download data as well as communicate with the users and/or adjust the sensor 200) and contains algorithms pre-stored for use (downloaded) by the users. The database in the network is used to store all the users (patient's data) including but not limited to (1) user/patient's profile data, (2) user/patient's movement and alert data and (3) user/patient's other data (neuromuscular electrical stimulation (NMES), algorithms, other sensor data, or any other data).

When compared to standard TED stockings and SCDs, embodiments of the present disclosure leverage the distinct advantages of monitoring mobility/immobility via an accelerometer and/or monitoring orientation via a gyroscope. That is, the relative motion and position of the patient wearing the sensor 200 can be monitored to track whether they may be at a higher risk for DVT/PE by their relative mobility/immobility.

The alert by the sensor 200 is designed to allow the wearer to determine whether they have been immobile or insufficiently mobile for a threshold period. For example, the alert can vibrate after a given period of time (for example, approximately ten minutes, fifteen minutes, thirty minutes, one hour) of immobility detected by the accelerometer. Similarly, an auditory alert can be included to allow the wearer, as well as any caretaker within earshot of the wearer, to determine that the wearer has been immobile for a threshold period. For example, the alert can beep after a given period of time (for example, approximately ten minutes, fifteen minutes, thirty minutes, one hour) of immobility detected by the accelerometer. This combination of vibratory and auditory alert systems acts as an efficient system to minimize patient immobility, thereby minimizing vascular stasis and reducing the risk of developing DVT. Other methods to alert the user can also be used, for example communicating to a device 260 which can then alert the user.

Examples of the present disclosure also leverage connectivity features that allow the sensor 200 to communicate patient activity data to another mobile device through BLUETOOTH and/or cloud computing. The connectivity of the sensor 200 allows the wearer, their care takers, and their healthcare providers to not only monitor the activity level of the wearer, but also allows everyone within this network (patient, care taker, healthcare personnel, etc.) to communicate with one another. For instance, if the patient has remained immobile for a given period of time (for example, approximately ten minutes, fifteen minutes, thirty minutes, one hour), an alert can be sent to the patient's care taker and/or healthcare provider to prompt them to remind the patient to either perform exercises designed to minimize the chances of developing DVT (for example, calf exercises) or mobilize themselves by getting up and ambulating, if they can do so. Over time, this data can be tracked, and data analytics can be employed to determine other risk factors for DVT. Further, if the user's condition has changed, such that a different threshold is applicable, then the wearer, care takers, and/or healthcare providers may be able to adjust the threshold to alert the user.

FIGS. 3A-3F show different views of an exemplary sensor 200 used in the exemplary system of FIG. 2, arranged in accordance with at least some embodiments described herein. In this example, the exterior of the sensor 200 can include a case top 201, a case bottom 202, a button 203, an on/off switch, speaker holes 204, and a battery door latch 205. The interior of the sensor may include an accelerometer, a gyroscope, a battery, a BLUETOOTH radio, a circuit board, a speaker, and a vibration chip. The button 203 can serve as an on/off switch. The button 203 can also function as a silencing button to turn off the alert. In other examples, the button 203 can be used for any suitable function.

The sensor 200 may include an accelerometer capable of detecting minute muscular movement, as well as built-in sound and vibration functions to alert the patient. The gyroscope can detect orientation of the user. Together with the accelerometer, the sensor 200 can calculate whether the user has moved in terms of degree and/or amount. The sensor 200 may also include a rechargeable/replaceable battery such as a lithium-cell battery, as well as an on/off switch for sleep mode.

In addition, the sensor 200 may include a built-in BLUETOOTH radio for wireless communication with other devices 260 such as a smartphone (for example, iPhone or Android phone), a handheld PC (for example, iPod Touch), a tablet computer (for example, iPad or Surface Pro), a laptop computer (for example, MacBook or Surface Book), a desktop computer, or any other suitable device. These mobile devices may include mobile applications (for example, smartphone apps) that can sync and store patient data via cloud services. The mobile applications may utilize a simple and/or intuitive user interface for ease of use. The sensor 200 can also include means to connect to the Internet, or cloud computing. The sensor 200 can also include ways to connect to power, such as a plug or a USB outlet, such that the sensor 200 can be plugged directly to a power source and/or a device 260.

Figure 4:
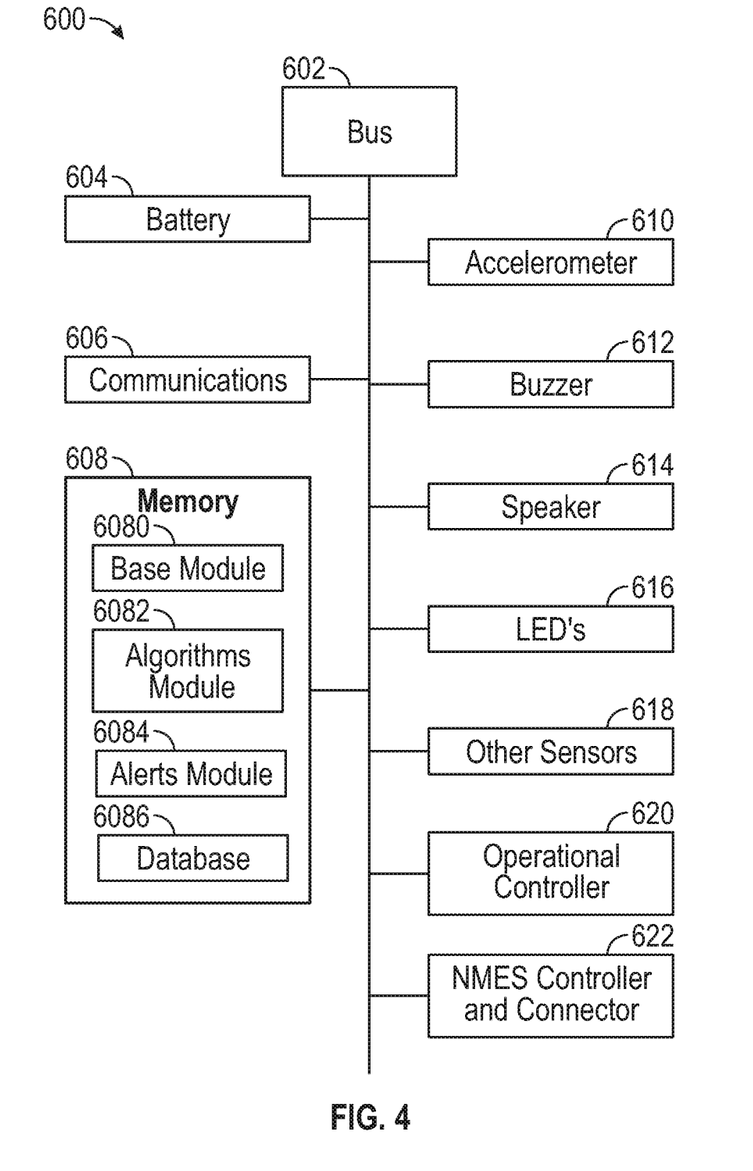
FIG. 4 shows an exemplary user interface of a mobile application by which at least aspects of monitoring and promoting patient mobility may be implemented.

FIG. 4 is a diagram 600 of an exemplary sensor. A bus 602 can be an electronic communication system that transfers data between components. A battery 604 can be a chargeable or rechargeable battery. Communications 606 can be any suitable radio, such as BLUETOOTH, Wi-Fi, ZigBee, or 3G/4G radio. Memory 608 can have a plurality of programs or modules and includes instructions to perform functions. The base module 6080 can control normal operating functions, such as (1) inputting any of the sensors to memory and storing to database, (2) interacting with operational controller that interprets and executes base software commands, such as (initial buzzer 612 for 5 seconds), (3) running algorithms on the data in the database to calculate movements and calculates when alerts are made, and (4) interacting with communications to input or output data to database. The alerts module 6084 is a software module that determines from either the data in the database or the algorithms to create alerts (sound or buzzer 612 or lights or other). The alerts module 6084 can send the alarms out and wait until either a period or until an amount of movement is detected.

The alerts module 6084 can further initiate a neuromuscular electronic stimulation (NMES) unit through a NMES controller 622. NMES units function as a muscle stimulator. The NMES unit sends electrical pulses from an externally applied source. The pulses stimulate targeted muscles to contract repeatedly over a specific period of time.

The accelerometer 610 detects movement in X, Y and Z axis. X axis can be defined as a movement along a direction, and Y axis can be defined as a movement orthogonal to the X axis. The X and Y axis are in the same plane. Z axis is orthogonal to the plane formed by the X and Y axis. As such, the X, Y, and Z axis provides three dimensions of movement. The accelerometer can be any of those known in the art and that can detect human being level movement.

The operational controller 620 is any of a type of micro controllers chosen from manufacturers, cores, data bus width, clock speed, RAM size, program memory size required to interoperate with all the devices and memory and battery.

Other sensors 618 can be any other sensors that may help to treat DVT users, such as (1) external accelerometer data from wearables that can detect motion of other parts of the body, (2) geo location that may correlate with movement, (3) external medical data, such as blood pressure or heart rate or ECG, EKG, (4) orientation such as a gyroscope, or any other suitable attribute.

The alerts module 6084 can also be a program that inputs any other sensors 618 that can alert the users based upon (1) external accelerometer data from wearables that can detect motion of other parts of the body, (2) geo location that may correlate with movement, (3) external medical data, such as blood pressure or heart rate or ECG, EKG, or any other suitable attribute.

Alerts module 6084 can also be used to trigger the NMES controller 622, (energy, time etc.) based upon (1) lack of movement or (2) independent of movement.

The alerts module 6084 can be downloaded from the application based upon the user configurations. The base module 6080, alerts module 6084, and algorithm module 6082 can be used to measure accelerometer and alert independent of communicating with the application. As such, the sensor can function without a device if desired.

Figure 5A:
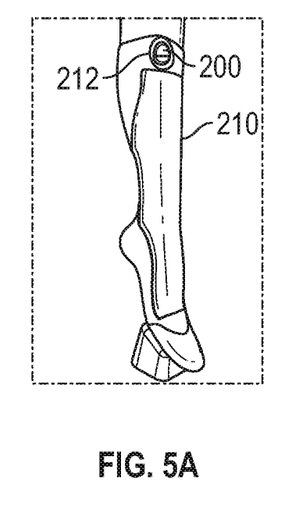
FIGS. 5A-5D show exemplary sensors and wearables by which at least aspects of monitoring and promoting patient mobility may be implemented.
Figure 5B:
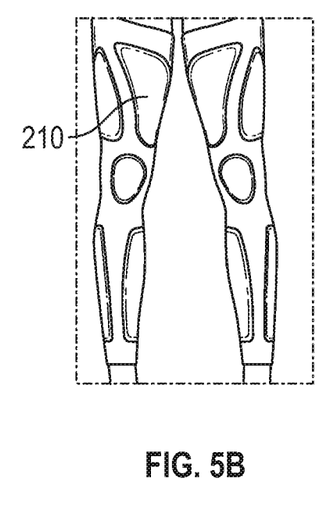
Figure 5C:
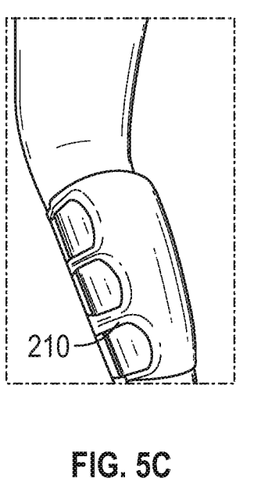
Figure 5D:
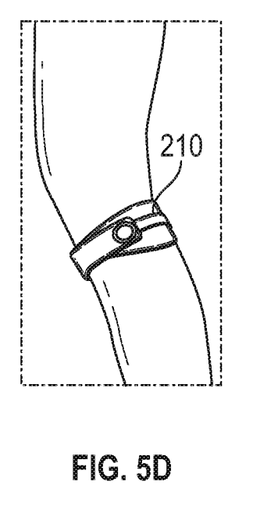

FIGS. 5A-5D illustrate examples of sensor 200 placed in a wearable 210. FIG. 5A shows a sensor placed in a compartment 212 of a wearable 210; in the illustrated example, a compression sock is shown. FIG. 5B shows another example of a wearable 210; in the illustrated example, a compression sleeve is shown. FIG. 5C illustrates an example of a wearable 210; in the illustrated example, the compression sleeve is only provided along the shin and calf of the user. FIG. 5D illustrates another example of a wearable 210; in the illustrated example, a band is shown. Other exemplary wearables 200 of different shapes and sizes can also be used in connection with a sensor 200. Also, while the sensors 200 may be placed in a compartment 212 of a wearable 210, the sensor 200 may also be built into a wearable 210.

Figure 6A:
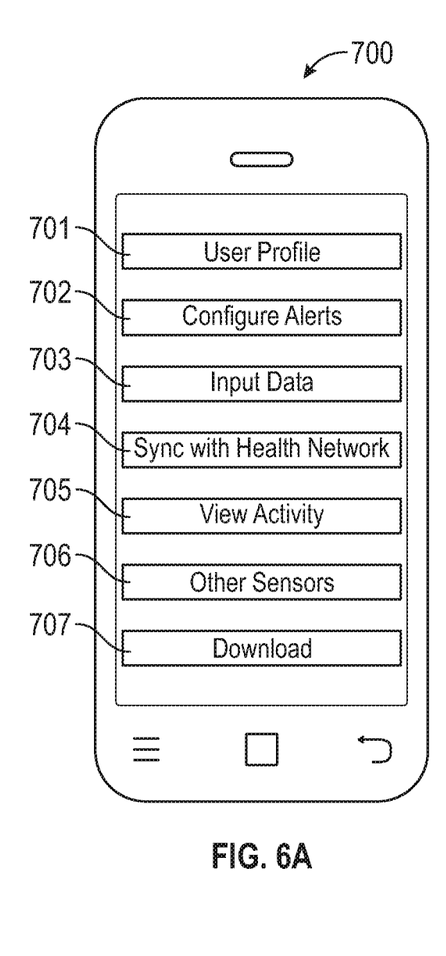
FIGS. 6A-6C show exemplary screens of a user interface of an application for a device that communicates with sensors, wearables, cloud computing, and a health network.
Figure 6B:
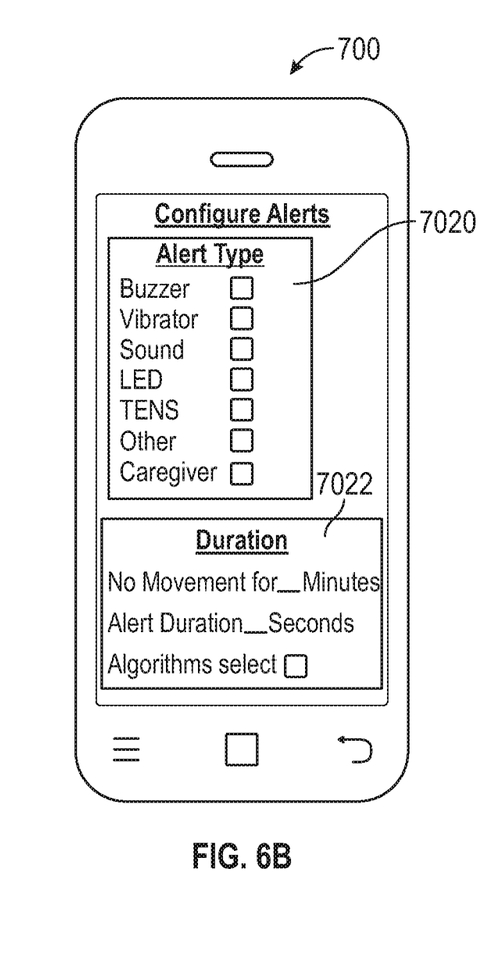
Figure 6C:
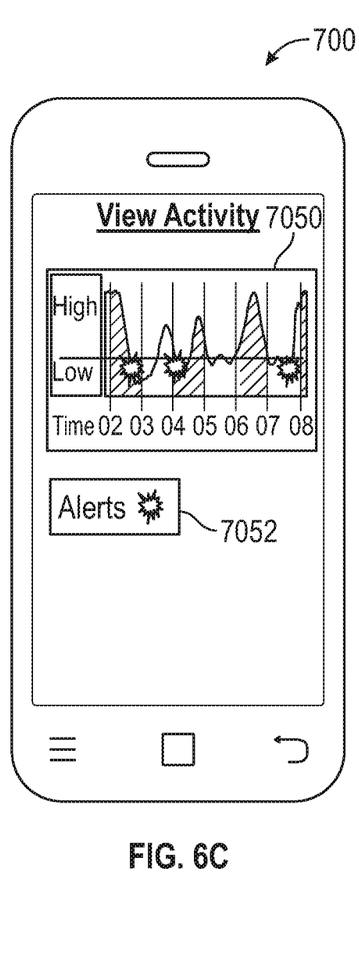

FIGS. 6A-6C shows an exemplary user interface of a mobile application 700 used in the example system of FIG. 2. In the illustrated example, the sensor 200 may transmit data to devices 260 via any suitable method, for example BLUETOOTH technology. The reminder features of the sensor 200 can be customized via an application 700 on a device 210 (for example, sound, vibration, alert timer, sleep mode). The application 700 can also alert authorized recipients of the patient's inactivity via email, text message, automated phone call, or any other suitable method of communication. The application 700 can also summarize the patient's activity data (hourly, daily, weekly, monthly, etc.) and provide the summary to the patient and authorized recipients. The data can be uploaded to a HIPAA-compliant cloud service for all authorized users (for example, physicians, family, care takers, etc.) to monitor. The authorized users could also utilize the application 700 to adjust the threshold to alert the user for mobility based on algorithms calculating attributes, for example the amount and degree of movement over a period of time.

The application 700 can be controlled by any suitable means. For example, the application 700 can be controlled through a touch screen. In other examples, the application 700 can be controlled by a mouse and keyboard.

FIG. 6A shows an example of a user interface that allows a user to create a user profile 701. The user profile 701 may include user personal information, email, text, phone, and any other information about the user that is deemed relevant. The user profile 701 may also include doctors and caregiver's information. The user profile 701 may also include certain medical algorithms to set up and use the sensor and alarms.

The user interface of the application 700 allows a user to configure alerts 702, which is shown in FIG. 6B. The user can select any of an alerts types, on the sensor buzzer, vibrator, sound LED, NMES or can contact the other devices or caregivers (Health Network).

FIG. 6B also shows an example of a user interface that allows a user to fill in and/or adjust the time that the alert would go off after no or not sufficient movement is detected 7022. The user interface of the application 700 allows a user to fill in the duration of the alert 7022. Further, FIG. 6B shows a user interface that allows a user to select an algorithm to use 7022, for instance, (1) amount of time no movement from X, Y and Z axis, (2) amount of time from inactivity of any one of X, Y, or Z axis, (3) amount of time of a given position (for example X,Y, movement, no Z axis, that is bed resting, (4) an algorithm that calculates a period of inactivity with active periods, such as an "activity duty cycle", (5) an algorithm that is based upon "slopes of inactivity", that is a downward trend of inactivity, (6) a set of timers that check in to see if there is activity within a window of a timer, or any other suitable algorithm.

As shown in FIG. 6A, a user can also input data 703 through the application 700. The user can input various alert algorithms of how to determine alerts. The user can input doctors or caregivers alert conditions. A user can input data to control the optional NMES components. The user can input other sensor data; for instance the user can input other user wearables communications to use other wearables data to help trigger alarms of NMES unit.

Also, FIG. 6A shows a user interface that allows a user to sync with Health Network 704 through the application 700. The user can set up the connection to the health network to upload or download data, to communicate with doctors or caregivers. The user can synchronize all movements and lack of movements and when alerts were sent. Based upon the number of alerts or time of day or amount of "other sensor" data, the user can set up times to synchronize data to the health network.

Through the application, a user can view activity 705, which is shown in FIG. 6C. As illustrated in the example shown in FIG. 6C, the user can see, by hours, the activity, where activity level form high to low. The low setting is selectable by the user or is downloadable by the Health network that will trigger an alert. In this way, a user can select, as in FIG. 6B, either no movement for a time, or can select the threshold to be an actual level or amount of movement which can trigger an alert. Alerts 7052 can be shown graphically on the view activity user interface.

As shown in FIG. 6A, the user interface allows a user to enable "other sensors," 706 through the application 700. The user can define what other sensors, besides the sensor attached to the wearable, should be enabled to help with alerts. Other sensors 706 include but are not limited to wearables for heart sensors, wearables for body temperature, wearables for activity, or other suitable sensors.

The user interface also allows a user to download data 707 through the application 700. When selected, the application 700 can download data from the sensor 200, after the sensor 200 was operating independently and not connected to a device 260.

Figure 7:
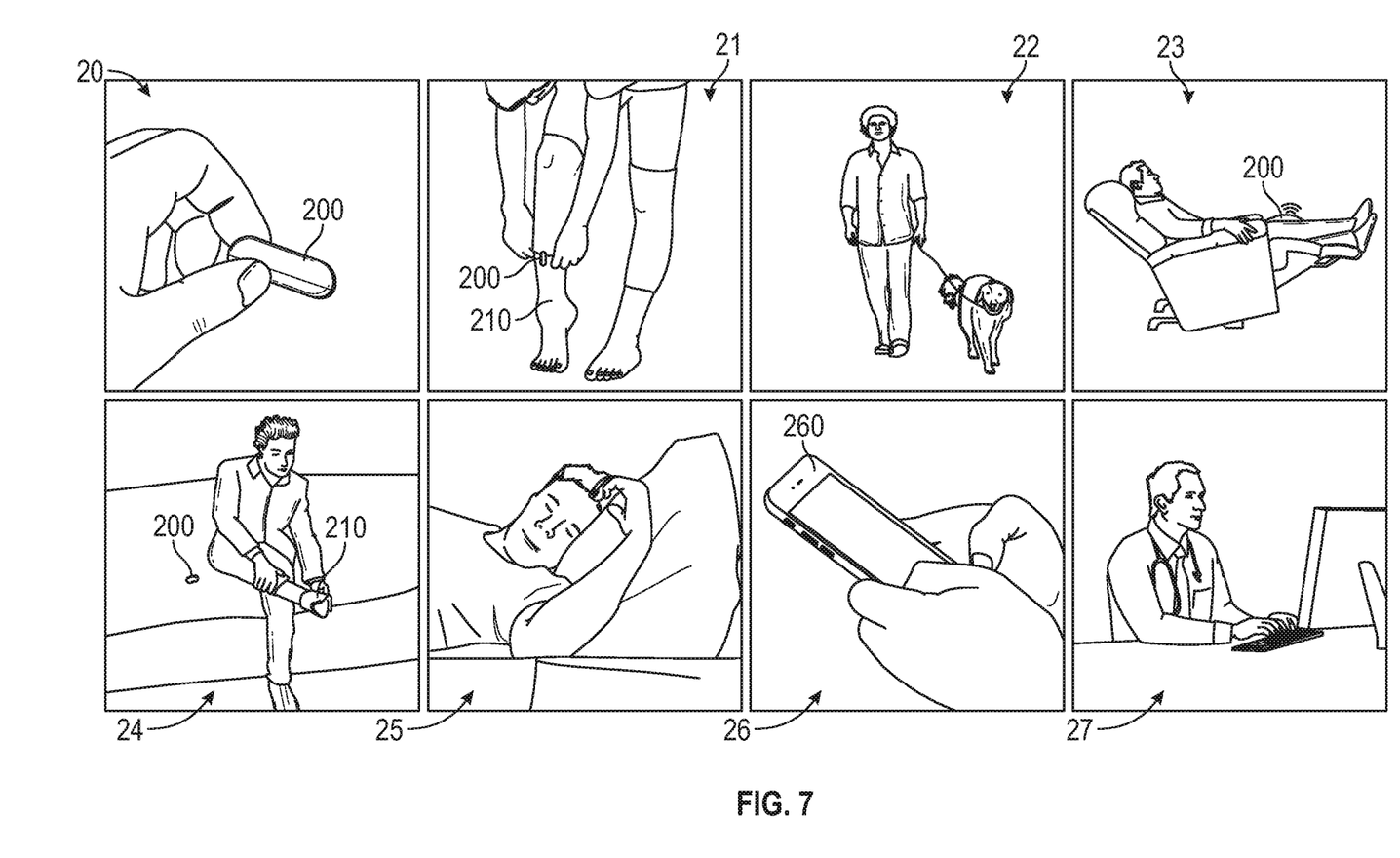
FIG. 7 shows an exemplary system by which at least aspects of monitoring and promoting patient mobility may be implemented.

FIG. 7 shows an exemplary system by which at least aspects of monitoring and promoting patient mobility may be implemented, arranged in accordance with at least some embodiments described herein. In this example, a set of pictures 20, 21, 22, 23, 24, 25, 26, 27 are used to demonstrate a user method to use a sensor, or a wearable, for use with a compression sleeve and mobile device.

In the first picture 20, a user holds a sensor 200 ready to insert into a wearable 210, for example a compression sleeve or a compression sock. In other examples, the sensor 200 can be built into the wearable 210, for example a band that can be worn around the ankle or wrist. The sensor 200 and/or the wearable 210 can also be used to communicate with other features, for example GPS, mobile devices, cloud computing, or any other features. In yet other examples, the sensor 200 and/or the wearable 210 can perform at least one function, for example measure heart rate, measure time, assess acceleration, assess velocity, and assess orientation. In the second picture 21, a user attaches the sensor 200 into the wearable 210, which, in the illustrated example, is a compression sock/sleeve. The sensor 200 can be inserted and/or attached to the wearable 210 by, but is not limited to, (1) having a small holder or pocket in the wearable 210 adapted to fit the sensor 200, (2) having the sensor 200 fit snugly under the wearable 210 without a holder, (3) having a fabric attachment (for example, Velcro), with one attachment coupled with the sensor 200 and one attachment coupled with the wearable 210, and (4) having the wearable 210 have a split opening capable of receiving the sensor 200. In the third picture 22, the user can move in normal daily activity. The sensor 200 tracks and calculates the movement of the user. In the fourth picture 23, the user is alerted by the sensor 200. The alert can be, but is not limited to, normal means of alerts, including (1) vibration of the sensor 200, (2) sounds on the sensor 200, (3) lights on the sensor 200, (4) communication to an alert on the mobile device via a text, audible or vibration alarm, email message, or any other method to alert the user. The fifth picture 24 shows the user removing the sensor 200. The user can, for example, remove the sensor 200 at the end of the day. In other examples, the user does not remove the wearable 210. If, for example, the wearable 210 is a band and not a compression sleeve, the user may keep the wearable 210 on at nearly all times. The sixth picture 25 shows the user sleeping. In at least one example, the user may still have the sensor 200 on and/or activated to track the user's movement. The tracking may help track the user's sleep patterns. In other examples, the user may have removed or deactivated the sensor 200 from alerting the user so as to not disturb the user's sleep. The seventh picture 26 shows a user downloading and initiating an application on a device 260. The sensor 200 and/or the wearable 210 may communicate with the device 260 and provide information therefrom. In at least one example, the device 260 can be a mobile device. In other examples, the device 260 can be any suitable device, for example a computer, to communicate with the sensor 200 and/or the wearable 210 such that the device 260 can provide information to the user and/or communicate with the Internet or other devices. The application can be a browser based application or an installed application. The data from the sensor 200 can be uploaded to the application. In the eighth and final picture 27, the data (from the sensor 200 and/or the wearable 210) on the device 260 in the application is uploaded to a professional (doctor, nurse, caregiver, etc.). The software for the application is provided so that a patient's mobility can be tracked, and notifications can be provided, if there is a concern with the lack of mobility. This system connects patients, family, caregivers, and doctors together and provides comprehensive user data. As such, the professional can help track the user's movement and, if needed, adjust a threshold to alert the user when movement is needed. The threshold may be based on features, such as time and movement. The movement may be the amount of movement and/or the degree of movement. Other features may be provided to be able to calculate the appropriate threshold for the user. To adjust the threshold to alert the user, the professional can adjust the application which passes the information back to the device 260, or directly to the sensor 200 and/or wearable 210.

In the illustrated example in FIG. 7, the smart device or sensor 200 may include the following features: 1) a wearable 210, such as band or a compression sock or sleeve, that allows the wearer to remain mobile; 2) an accelerometer to measure the mobility/immobility of the wearer; 3) a gyroscope to measure the orientation of the wearer; 4) an alert system to notify the wearer, caretaker, and/or healthcare personnel of the wearer's relative immobility; 5) the ability of the sensor 200 and/or the wearable 210 to communicate the information regarding the wearer's activity with another device 260 (for example, smartphone, tablet, computer, or any other device) via direct connection, as USB, or wireless connection such as BLUETOOTH, cloud computing and/or any other suitable means for transferring information and data from one device to another.

The exemplary system can alert patients to mobilize when immobility has been detected for a given period of time (for example, approximately ten minutes, fifteen minutes, thirty minutes, one hour). The system can also alert patients to mobilize when the degree of movement is not sufficient for a given period of time. The system can notify caregivers, family, and doctors to assist and take actions if necessary to help. The system can also provide the caregivers, family, and doctors to adjust the threshold for activity to alert the user. An activity summary can be sent wirelessly to physicians providing a more complete picture in assessing the progress of their patients' rehab. The activity summary can also be provided directly to the user.

The exemplary system shown in FIG. 7 may include wearables 210, such as knee-high gradient compression socks or sleeves (for example, approximately 20-40 mmHg) to decrease/prevent swelling, and to prevent fluid from pooling in the ankle, calf, and thigh. The patient may wear the compression socks as instructed by the physician and can be worn at all times. As illustrated in FIG. 2, the sensor 200 may be placed in a pocket located in the top-front of the compression sock, or on the right or left side of the compression sock depending on physician recommendation. The sensor 200 should not be placed in areas that could create pressure points on nerves or blood vessels, and may be placed on the outside of the compression sock to avoid direct skin contact, due to concerns of discomfort and skin allergies.

Figure 8:
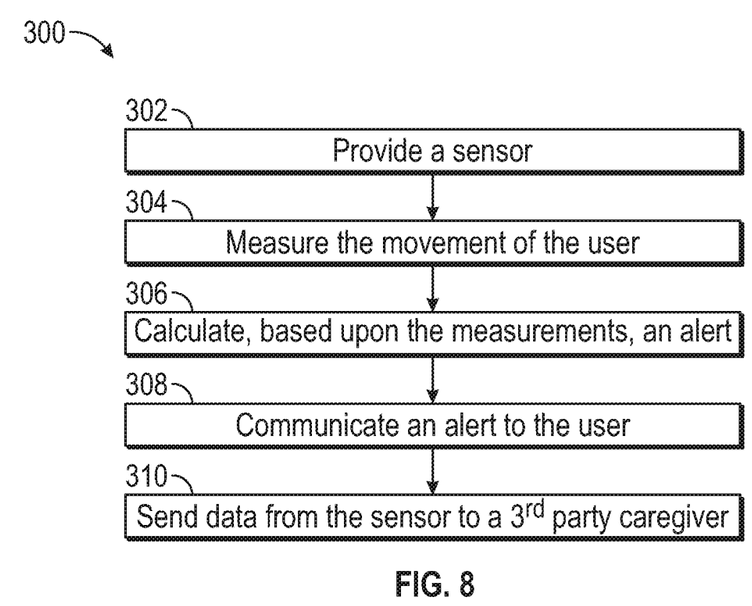
FIG. 8 shows an example method of a system by which at least aspects of monitoring and promoting patient mobility may be implemented, all arranged in accordance with at least some embodiments described herein.

Referring to FIG. 8, a flowchart is presented in accordance with an example. The example method 300 is provided by way of example, as there are a variety of ways to carry out the method 300. The method 300 described below can be carried out using the configurations illustrated in FIGS. 1-7, for example. Each block shown in FIG. 8 represents one or more processes, methods or subroutines, carried out in the example method 300. Furthermore, the illustrated order of blocks is illustrative only and the order of the blocks can change according to the present disclosure. Additional blocks may be added or fewer blocks may be utilized, without departing from this disclosure. The example method 300 can begin at block 302.

At block 302, a sensor is provided which is operable to measure movement and alert a user. In at least one example, the sensor can also communicate with a device or cloud computing. The sensor can be a small clam shell package with a small battery operated component that has an accelerometer component and/or a gyroscopic component for measuring movement, optionally a vibrator component for alerts, optionally LEDs component for alerts, optionally a speaker or buzzer component for alerts and a communications component (for example BLUETOOTH device) and optionally a memory component and a controller component for controlling all these components.

A device with an application operable to communicate with the sensor is also provided. The device can be, for example, a smart phone, a tablet, or a computer. The application can communicate with the sensor to extract movement data, allow the user or caregiver to set and/or adjust alerts, and when needed provide alerts either to the user's sensor or another device, for example a care giver's device.

The sensor can be inserted into, or built into, a wearable. The wearable can be, for example, a compression sock, a compression sleeve, or a band. The user can (1) have a small holder, compartment, or pocket in the wearable configured to retain the sensor, (2) have the sensor fit under the wearable without a holder, (3) have a fabric attachment (for example Velcro) one attachment coupled with the sensor, one attachment coupled with the wearable, and (4) have the wearable have a split opening capable of receiving the sensor.

With the wearable on and the sensor retained therein, the user can move in normal movement. The accelerometer in the sensor can determine if any movement is made or can detect any appreciable movements in X, Y, and Z axis.

At block 304, the movement or activity of the user is measured by the sensor. Data reflecting the measurements can be sent to a device, which can be accessed by the user, care givers, doctors, and/or any authorized user through an application. The data can be sent either directly, for example USB, or wirelessly, for example WiFi, cloud computing, BLUETOOTH. The data can be sent to the device from the sensor in real time or can be sent to the user when fetched from the memory of the sensor (if the accelerometer data is stored optionally in memory). The data may also be sent from the sensor to the device at predetermined times scheduled by the device through the application or may be sent only when the sensor and the device are in range. Any other suitable methods or times of communicating the data from the sensor to devices can be used.

At block 306, an alert is calculated based on the measurements. The alert can be created based upon a number of factors, for instance, (1) amount of time no movement from X, Y and Z axis, (2) amount of time from inactivity of any of X, Y, or Z axis, (3) amount of time of a given position (for example movement in X and Y axis, but no movement in Z axis, which can, for example, equate to bed resting), (4) an algorithm that calculates a period of inactivity with active periods, such as an "activity duty cycle", (5) an algorithm that is based upon "slopes of inactivity", that is a downward trend of inactivity, (6) a set of timers that check in to see if there is activity within a window of a timer, or any other suitable algorithm. The alert can be calculated at the sensor, at a device through an application, or calculated through an application provided in cloud computing.

At block 308, an alert is communicated to a user. The alert can be programmed as any possible alert (sounds, vibration, buzzers, lights) provided on the sensor itself, alerts through the application and connected devices (buzzers, vibrators, lights, text, emails etc.), or a combination thereof. Also, the alerts can be sent to and from a caregiver or authorized user through the application.

Alerts can be coded in either time, or amounts of intensity or amounts in coded (on/off/on) etc. Each alert can recommend to (1) be active again, (2) to speed up, (3) to do an exercise, (4) to move in position (sit to stand), (5) to move in sync with another sensor (for example heart rate), or any other suitable recommendation.

At block 310, the user can send data from the sensor to the application of a third party caregiver. In this step the 3rd party could be a remote doctor, caregiver, nurse, relative or could be a cloud network that stores the data or analyzes the data, or any authorized users. Third parties can access the application and adjust the threshold for alerts as needed. For example, if the user's medical situation changes, the authorized user can adjust the application to change the threshold for alerts.

In an illustrative example, any of the operations, processes, etc. described herein can be implemented as computer-readable instructions stored on a computer-readable medium. The computer-readable instructions can be executed by a processor of a mobile unit, a network element, and/or any other computing device.

There is little distinction left between hardware and software implementations of aspects of systems; the use of hardware or software is generally (but not always, in that in certain contexts the choice between hardware and software can become significant) a design choice representing cost vs. efficiency tradeoffs. There are various vehicles by which processes and/or systems and/or other technologies described herein can be effected (for example, hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; if flexibility is paramount, the implementer may opt for a mainly software implementation; or, yet again alternatively, the implementer may opt for some combination of hardware, software, and/or firmware.

The foregoing detailed description has set forth various embodiments of the devices and/or processes via the use of diagrams and/or examples. Insofar as such diagrams and/or examples contain one or more functions and/or operations, it will be understood by those within the art that each function and/or operation within such diagrams or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (for example, as one or more programs running on one or more computer systems), as one or more programs running on one or more processors (for example, as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the signal bearing medium used to carry out the distribution. Examples of a signal bearing medium include, but are not limited to, the following: a recordable type medium such as a floppy disk, a hard disk drive, a CD, a DVD, a digital tape, a computer memory, etc.; and a transmission type medium such as a digital and/or an analog communication medium (for example, a fiber optic cable, a waveguide, a wired communications link, a wireless communication link, etc.).

Those skilled in the art will recognize that it is common within the art to describe devices and/or processes in the fashion set forth herein, and thereafter use engineering practices to integrate such described devices and/or processes into data processing systems. That is, at least a portion of the devices and/or processes described herein can be integrated into a data processing system via a reasonable amount of experimentation. Those having skill in the art will recognize that a typical data processing system generally includes one or more of a system unit housing, a video display device, a memory such as volatile and non-volatile memory, processors such as microprocessors and digital signal processors, computational entities such as operating systems, drivers, graphical user interfaces, and applications programs, one or more interaction devices, such as a touch pad or screen, and/or control systems including feedback loops and control motors (for example, feedback for sensing position and/or velocity; control motors for moving and/or adjusting components and/or quantities). A typical data processing system may be implemented utilizing any suitable commercially available components, such as those typically found in data computing/communication and/or network computing/communication systems.

The herein described subject matter sometimes illustrates different components contained within, or connected with, different other components. It is to be understood that such depicted architectures are merely examples, and that in fact many other architectures can be implemented which achieve the same functionality. In a conceptual sense, any arrangement of components to achieve the same functionality is effectively "associated" such that the desired functionality is achieved. Hence, any two components herein combined to achieve a functionality be "associated with" each other such that the desired functionality is achieved, irrespective of architectures or intermedial components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include but are not limited to physically mateable and/or physically interacting components and/or wirelessly interactable and/or wirelessly interacting components and/or logically interacting and/or logically interactable components.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (for example, bodies of the appended claims) are generally intended as "open" terms (for example, the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (for example, "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (for example, the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (for example, "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (for example, "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims.

The invention claimed is:

1. A method, comprising:
    connecting a sensor to a device that is communicatively connected to, at least, a cloud-based network;
    receiving, at the device, a configuration defined by a user, wherein the configuration includes:
        (a) at least one alert selected from a plurality of alert types, wherein at least one of the alert types is neuromuscular electrical stimulation (NMES),
        (b) a time period of insufficient movement for triggering the at least one alert, and
        (c) at least one algorithm selected from a plurality of different algorithms for calculating whether the time period of insufficient movement for triggering the at least one alert has elapsed;
    determining an adjustable sensor threshold compatible with the configuration defined by the user;
    measuring movement of the user over time with the sensor;
    transmitting the measured movement, via the device, to the cloud-based network for potential adjustments to the adjustable sensor threshold;
    determining whether the measured movement over time is below the adjustable sensor threshold;
    when the measured movement over time is below the adjustable sensor threshold, activating an alert unit in accordance with the configuration defined by the user wherein if the selected at least one alert is NMES, the alert unit is configured to trigger a NMES unit to generate a NMES signal to stimulate targeted muscles on the user.

2. The method of claim 1, further comprising receiving, at the device, an adjustment to the adjustable sensor threshold from the cloud-based network when the measured movement over time is below the adjustable sensor threshold.

3. The method of claim 2, wherein the adjustment is received from a remote device connected to the cloud-based network, the remote device being associated with an authorized third party user.

4. The method of claim 3, wherein the device is configured to adjust the adjustable sensor threshold according to the adjustment received from the cloud-based network.

5. The method of claim 1, wherein the device is one or more of a smartphone, a handheld PC, a tablet computer, a laptop computer, or a desktop computer.

6. The method of claim 1, wherein the sensor is coupled with a wearable, wherein the wearable is at least one of a band, a compression stocking, or a compression sleeve.

7. The method of claim 1, wherein the alert unit produces at least one of: a sound, a vibration, or a combination thereof.

8. The method of claim 1, wherein the determining of whether the measured movement over time is below the adjustable sensor threshold is performed at the sensor.

9. The method of claim 1, wherein the sensor comprises an accelerometer.

10. The method of claim 1, further comprising presenting a user interface that includes a display for receiving the configuration defined by the user.

11. The method of claim 1, wherein the user selects the at least one algorithm from the plurality of different algorithms for calculating whether the time period of insufficient movement for triggering the at least one alert has elapsed.

12. A system, comprising:
    a device connected to a cloud-based network and configured to:
        receive measured movement over time of a user,
        present a user interface that includes a display for receiving a configuration defined by the user, wherein the configuration includes:
            (a) at least one alert selected from a plurality of alert types, wherein at least one of the alert types is neuromuscular electrical stimulation (NMES), (b) a time period of insufficient movement for triggering the at least one alert, and
(c) at least one algorithm selected from a plurality of different algorithms for calculating whether the time period of insufficient movement for triggering the at least one alert has elapsed,
transmit control signals based at least in part upon the configuration defined by the user, and
transmit the measured movement of the user over time to the cloud-based network for receiving potential adjustments to adjustable sensor threshold compatible with the configuration defined by the user; and
a sensor communicatively coupled with the device, the sensor comprising an alert unit and configured to:
determine the measured movement over time,
receive the control signals transmitted from the device, and
activate the alert unit when the measured movement over time is below the adjustable sensor threshold wherein activating the alert unit causes the alert unit to generate a NMES signal to stimulate targeted muscles of the user.

13. The system of claim 12, wherein the device is configured to receive an adjustment from the cloud-based network and adjust the adjustable sensor threshold according to the adjustment.

14. The system of claim 12, wherein the device is one or more of a smartphone, a handheld PC, a tablet computer, a laptop computer, or a desktop computer.

15. The system of claim 12, wherein the sensor is coupled with a wearable, wherein the wearable is at least one of a band, a compression stocking, or a compression sleeve.

16. The system of claim 12, wherein the alert unit produces at least one of a sound or a vibration.

17. The system of claim 12, wherein the sensor comprises an accelerometer.

18. A sensor system operable to measure movement over time of a user, the sensor system comprising:
an alert unit;
a neuromuscular electronic stimulation (NMES) unit configured to send electrical pulses to a targeted muscle of the user;
an accelerometer;
a device connected to a cloud-based network and configured to present a user interface including a display for receiving a configuration defined by the user, wherein the configuration includes:
(a) at least one alert selected from a plurality of alert types, wherein at least one of the alert types is NMES,
(b a time period of insufficient movement for triggering the at least one alert, and
(c) at least one algorithm selected from a plurality of different algorithms for calculating whether the time period of insufficient movement for triggering the at least one alert has elapsed; and
a controller communicatively coupled with the device, the controller configured to:
receive, from the device, the configuration defined by the user,
activate the alert unit when the measured movement over time is below an adjustable sensor threshold compatible with the configuration defined by the user, and
trigger the NMES unit to send the electrical pulses to the targeted muscle of the user if the selected at least one alert is NMES.

19. The sensor of claim 18, further comprising a wearable, wherein the wearable is at least one of a band, a compression stocking, or a compression sleeve.

20. The sensor system of claim 18, wherein the adjustable sensor threshold is adjustable by the device according to an adjustment received from the cloud-based network.

21. The sensor system of claim 18, wherein the controller is configured to transmit an alert to the device or the cloud-based network when the measured movement over time is below the adjustable sensor threshold.

22. The sensor system of claim 18, wherein the alert unit produces at least one of a sound or a vibration.

* * * * *